United States Patent [19]

Forberg

[11] Patent Number: 4,540,027
[45] Date of Patent: Sep. 10, 1985

[54] CHECK VALVE FOR INFUSION AND TRANSFUSION APPARATUS

[75] Inventor: Hans J. Forberg, Damlos, Fed. Rep. of Germany

[73] Assignee: TRANSCODAN, Sven Husted-Andersen GmbH & Co. KG, Fed. Rep. of Germany

[21] Appl. No.: 533,000

[22] Filed: Sep. 16, 1983

[30] Foreign Application Priority Data

Sep. 17, 1982 [DE] Fed. Rep. of Germany ... 8226183[U]

[51] Int. Cl.³ .......................... F16L 11/00; A61M 5/14
[52] U.S. Cl. ...................................... 137/848; 604/247
[58] Field of Search ............................ 604/247, 9, 30; 137/846, 844, 855, 848; 251/149.8

[56] References Cited

U.S. PATENT DOCUMENTS

| | | | |
|---|---|---|---|
| 3,109,429 | 11/1963 | Schwartz | 604/247 |
| 4,005,710 | 2/1977 | Zeddies | 604/251 X |
| 4,063,555 | 12/1977 | Ulinder | 604/247 X |
| 4,232,677 | 11/1980 | Leibinsohn | 604/247 |
| 4,405,316 | 9/1983 | Mittleman | 604/247 X |
| 4,429,856 | 2/1984 | Jackson | 604/247 X |

Primary Examiner—Stephen C. Pellegrino
Attorney, Agent, or Firm—McGlew and Tuttle

[57] ABSTRACT

The check valve for infusion and transfusion apparatus comprises a hollow cylindrical member of elastic material which has an open end for the inflow of fluid and an opposite closed end. The hollow cylindrical member has a side wall with an incision in a portion thereof which extends into the hollow interior and provides a flow passage in a direction from the hollow interior outwardly of the cylindrical member. The cylindrical member advantageously has a flange at its entrance end which provides a means for mounting and supporting the valve member. The valve member may be disposed between two connected parts of a housing so that the flange is compressed therebetween and held in position. The construction is usable in a valve housing of a flexible line if the housing includes two interconnected parts which are assembled so as to hold the flange portion of the valve member therebetween. The part in question advantageously includes a flexible line which has a Y or similar connection or it may be arranged in a straight valve housing connection which for example may provide a cannula holder or a connection to the lower end of a drip chamber for example.

5 Claims, 8 Drawing Figures

CHECK VALVE FOR INFUSION AND TRANSFUSION APPARATUS

FIELD AND BACKGROUND OF THE INVENTION

This invention relates in general to valves and in particular to a new and useful check valve for infusion and transfusion apparatus.

In infusion and transfusion apparatus, it is known to insert check valves at various locations into the flexible line of the apparatus. The check valves are to prevent the fluid from returning into the flexible line in certain instances. It is known, for example, to insert check valves into the flexible lines which are connected to the run-off connection of drip chambers. It is further known to insert check valves into distribution pieces such as Y-pieces.

The prior art valves are designed as ball valves, disk valves, or as duck's bill valves. These valves are complicated and expensive to manufacture. They also have various drawbacks. For example, ball valves close tightly only in a conical seat. Then, however, there is a risk of the ball becoming stuck. Disk valves have the drawback of being very position dependent. Further, the valve disk may get stuck on the valve seat. The function of both these valves largely depends on the pressure or flow, i.e. they operate satisfactorily only at certain differential pressures or flow velocities. In duck's bill valves, the opening pressure is indefinite.

SUMMARY OF THE INVENTION

The invention is directed to a check valve which is as simple and reliable in operation as possible. The valve is most simple to manufacture. No particular difficulties arise with the mounting of the valve in the apparatus, and even unskilled persons are able to do it. The valve is further suitable for being mechanically fitted into apparatus provided therefor. The valve also is of a construction not requiring particular maintenance or monitoring.

To this end, the invention provides that the check valve is formed by a cup-shaped body, having its cylindrical portion above the bottom portion unilaterally cut through.

The inventive check valve has the advantage that it closes and opens satisfactorily independently of the flow velocity. In addition, it opens and closes under slight differential pressures. In its normal position the valve is closed. The valve operates independently of its position, always in the same way. The valve is simple in construction and, consequently, can be manufactured in a simple way, with simple tools. Further, the valve can be inserted into the respective apparatus by unskilled persons, or mounted mechanically.

The inventive check valve has the further advantage that in apparatus arrangements where additional solutions are introduced into a flexible line laterally, it prevents the solution from flowing back.

In a preferred embodiment of the invention, the check valve is inserted into a cannula holder. In another preferred embodiment, the check valve may be inserted in a casing having on one side a coupling connection or the cannula holder, and on the other side a connection for a cannula. A further preferred embodiment may have the check valve inserted directly in the connecting cone of the cannula. In these embodiments of the invention, a further advantage is obtained in the so-called pressure infusion. With this infusion, the liquid is introduced into the patient under increased pressure. If due to excess pressure, the flexible line ruptures or bursts, or if the connection between the infusion apparatus and the cannula is otherwise interrupted under effluence, the patient's blood may flow out through the cannula and the open way, and the patient may bleed to death.

Accordingly it is an object of the invention to provide an improved valve for infusion and transfusion apparatus which comprises a hollow cylindrical member of elastic material which has an opened end for the inflow of the fluid and an opposite closed end which has a side wall with an incision therein defined over a portion thereof which extends into hollow interior and provides a flow passage in a direction from the hollow interior outwardly.

A further object of the invention is to provide a check valve which includes a housing comprising two interconnecting parts and a check valve member having a flange portion held between the two parts which has an opposite closed end and an incision in a side wall which extends into the hollow interior providing for a continuation of flow from the interior through the incision.

A further object of the invention is to provide a check valve which is simple in design, rugged in construction and economical to manufacture.

The various features of novelty which characterize the invention are pointed out with particularity in the claims annexed to and forming part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
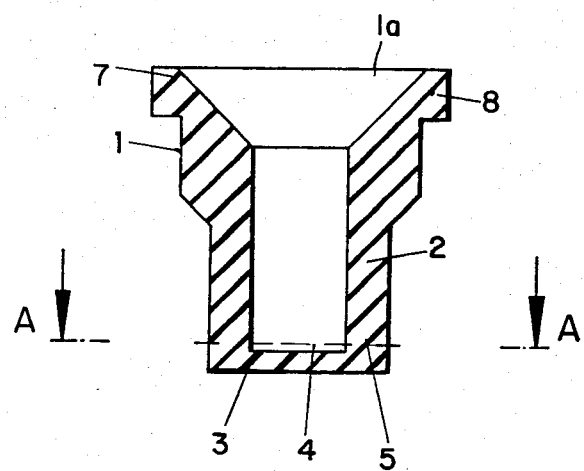
FIG. 1 is an enlarged sectional view of a valve constructed in accordance with the invention.

Referring to the drawings in particular the invention embodied therein comprises a cup-shaped check valve generally designated 1 which comprises a hollow cylindrical member having an open end 1a for the inflow of a fluid and an opposite closed end bottom portion 3. In accordance with the invention the valve includes a side wall or cylindrical portion 2, an incision 5 which extends from the exterior into the hollow interior of the valve body 1 and provides a flow of fluid from the interior to the exterior of the body.

Figure 2:
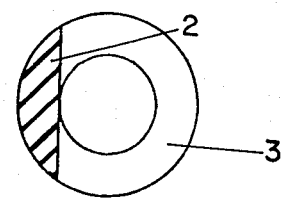
FIG. 2 is a section taken along the line A—A of FIG. 1.

The check valve 1 comprises a cylindrical portion 2 and a bottom portion 3. Cylindrical portion 2 is incised by a cut extending in the plane of the inside surface 4 of bottom portion 3. Cut or incision 5 extends into the cylindrical portion only partly, as shown in FIG. 2. The incision 5 lies in a plane which is parallel to the top surface of bottom portion 3 and at this top surface or slightly above the top surface. The incision extends through the inner and outer cylindrical surfaces of cylindrical portion 2, up to a line which is tangent to the inner surface as shown in FIG. 2.

Figure 4:
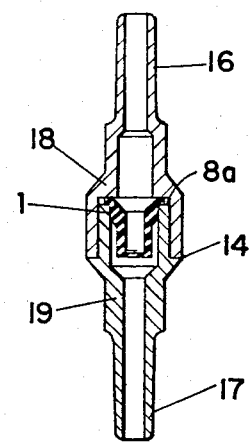
FIG. 4 is an enlarged sectional view of a portion of the valve shown in FIG. 3.

Cylindrical portion 2 is provided at its upper rim with a flange 8 which may have a tapering surface or conical rim 7 on its inside. The flange 8 serves the purpose of supporting the valve on a support shoulder 8a as shown in the respective apparatus part or housing as shown in FIG. 4.

Figure 3:
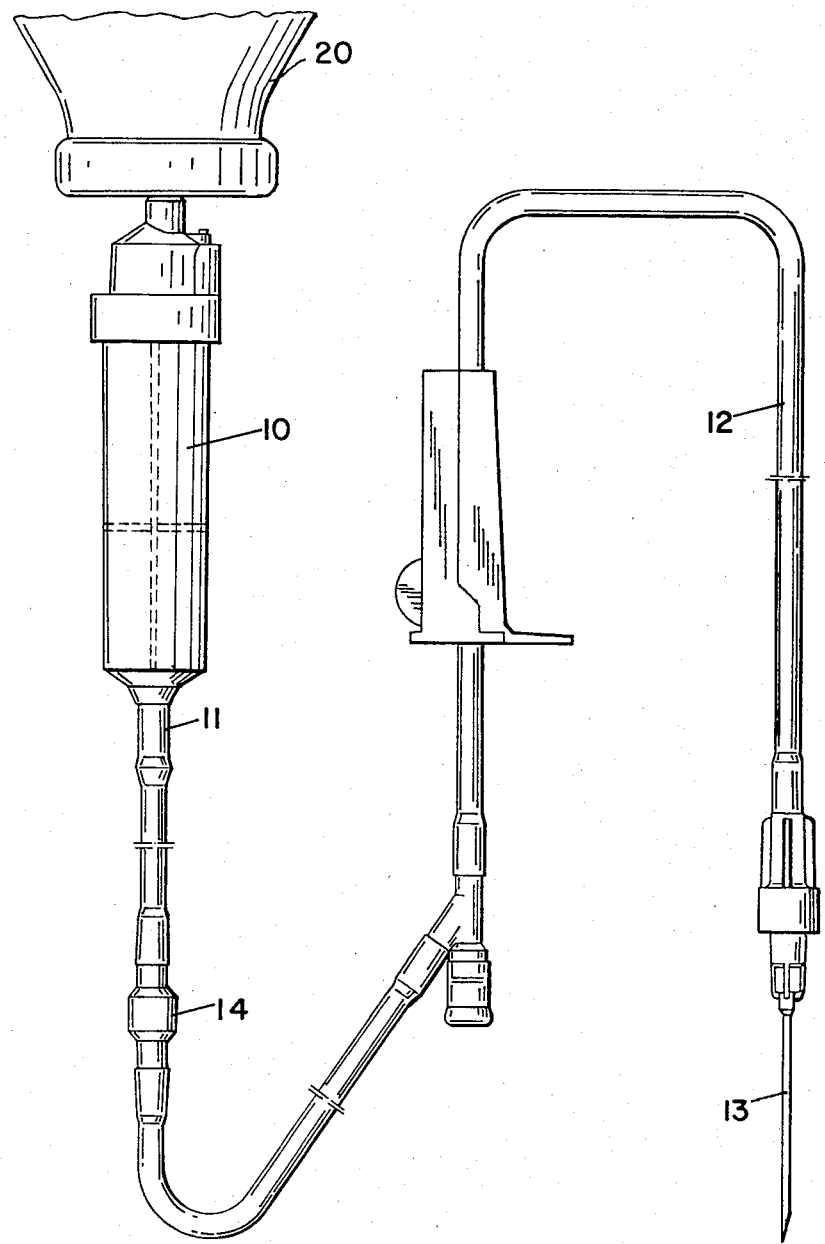
FIG. 3 is a diagrammatic view of an infusion transfusion apparatus having one or more portions with a valve therein constructed in accordance with the invention.

FIG. 3 illustrates, by way of example, an infusion transfusion apparatus comprising, among others, a drip chamber 10 having a run off connection 11. Drip chamber 10 is connected from below to the bottom seal of a supply vessel 20. From the drip chamber 10, a flexible tube 12 leads to a cannula 13 or a cannula holder. In the flexible tube 12 there is a housing or valve, a casing 14 with connections 16 and 17 as shown in FIG. 4, in which the check valve 1 is received. Casing 14 is made in two parts 18 and 19 which are joined to each other in a suitable manner.

The check valve closes instantly upon a reflux of the solution to be infused, irrespective of what the cause of this refluence is.

Figure 5:
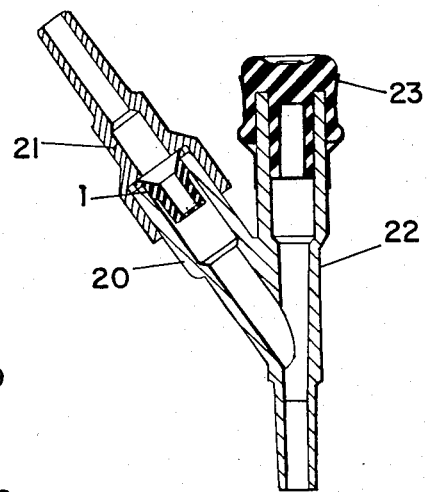
FIG. 5 is a view similar to FIG. 4 showing the valve in a Y connection.

In an embodiment according to FIG. 5, the valve is inserted in the connection 20 of a Y-piece. Instead of a Y-piece, another distributing fitting may also be employed. Here again, check valve 1 is tightly seated by means of its flange and held in place by means of a connecting piece which may be joined to the Y-piece in a manner known per se. on its other branch 22, the Y-piece carries a piercable cover-cup 23. Therethrough, additional infusion solutions, etc. may be introduced. Should the pressures in the interior exceed a certain level, check valve 1 closes and prevents the solution from returning into the drip chamber.

Figure 6:
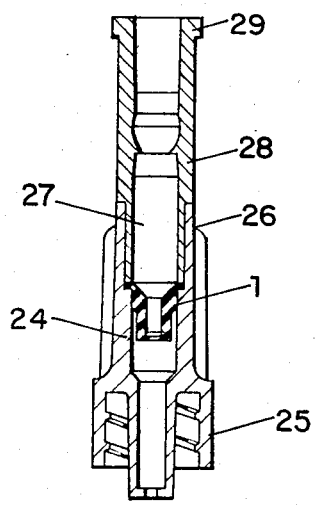
FIG. 6 is a view similar to FIG. 5 showing another embodiment of the invention.

FIG. 6 shows a cannula holder 24, which, in this embodiment, is provided with a locking connection 25 to which the connection of the cannula (not shown) can be screwed. The other end 26 of the cannula holder is provided with a bore 27 for inserting a check valve 1, again having a sealing flange and a connection 28 which in this embodiment is designed with a connecting portion 29 in the form of a cannula coupling element. This assembly therefore may further be inserted into a connecting one (not shown) of a cannula, which cone in turn is connected by its other end to the flexible tube leading from the drip chamber. Connection 28 may also be designed differently, for example as a length of a normal flexible tube to be connected to the flexible line leading from the drip chamber.

Figure 7:
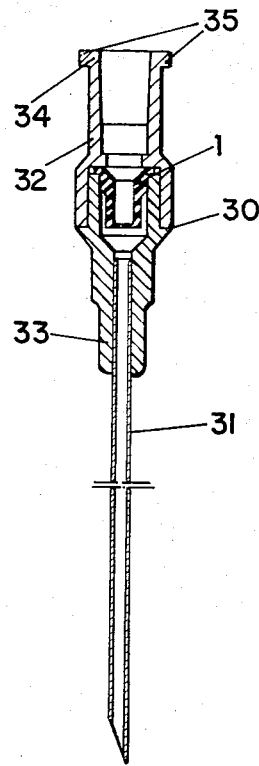
FIG. 7 is a view similar to FIG. 5 of still another embodiment of the invention.

FIG. 7 shows a valve 1 inserted in the connecting cone 30 of a cannula 31. Connecting cone 30 again comprises two parts 32 and 33 which are designed so as to have valve body 1 tightly seated by its connecting flange. On its connecting end 34, the cone is provided with two cogs 35 by which it may be engaged or screwed into locking connection 25 of the cannula holder.

Figure 8:
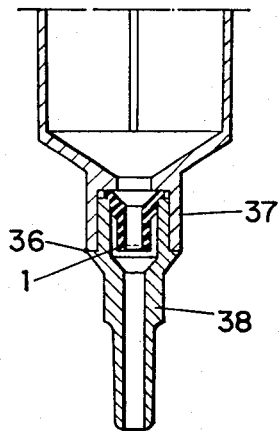
FIG. 8 is a view similar to FIG. 5 of still another embodiment of the invention indicating the valve on a portion of a drip chamber.

FIG. 8 shows check valve 1 inserted at a location 37 into the bottom portion 36 of a drip chamber. The check valve is held in place by a correspondingly shaped connection 38 for the flexible tube.

While specific embodients of the invention have been shown and described in detail to illustrate the application of the principles of the invention, it will be understood that the invention may be embodied otherwise without departing from such principles.

What is claimed is:

1. A check valve for infusion and transfusion apparatus, comprising a one piece hollow cylindrical member of elastic material defining a cylindrical hollow interior and having an open top end for the inflow of fluid and an opposite closed bottom portion, said bottom portion having a top surface in the hollow interior, said cylindrical member also having a side wall with cylindrical inner and outer surfaces and a planar incision extending into the hollow interior through the cylindrical inner and outer surfaces, up to a line which is tangent with the cylindrical inner surface, said incision providing a flow passage in a direction from the hollow interior outwardly, said planar incision lying in a plane closely adjacent and above the top surface of the bottom portion.

2. A check valve according to claim 1, wherein said hollow cylindrical member has a flange at its end adjacent said open end and wherein the open end has an interior surface with an inwardly extending conical surface.

3. A check valve according to claim 2, wherein the top surface of said bottom portion lies in a plane parallel to said planar incision, said planar incision extending radially to said cylindrical inner and outer surfaces, said bottom portion having a planar radially extending bottom surface.

4. A check valve according to claim 3, wherein said hollow cylindrical member includes a large diameter cylindrical portion between said flange and said sidewall, said large diameter portion having a diameter which is smaller than an outer diameter of said flange and which is larger than an outer diameter of said cylindrical outer surface of said sidewall, said hollow cylindrical member including a conical surface between said large diameter portion and said outer surface of said sidewall.

5. A check valve according to claim 4, including a two-part housing connected around said hollow cylindrical member, said two-part housing including a first part having an inner cylindrical surface engaged around an outer surface of said large diameter portion and defining a space for containing said sidewall of said cylindrical member, said first part having an end engaged with a lower surface of said flange, said housing having a second part with an inner diameter engaged around an outer diameter of said first part, said second part defining an interior with a support shoulder engaged against an upper surface of said flange.

* * * * *